(12) United States Patent
Perrin et al.

(10) Patent No.: US 6,342,396 B1
(45) Date of Patent: Jan. 29, 2002

(54) METHOD FOR ISOLATING, IN PARTICULAR FOR DETECTING OR QUANTIFYING AN ANALYTE IN A MEDIUM

(75) Inventors: Agnés Perrin, Lyons; Alain Theretz, Ecully; Bernard Mandrand, Villeurbanne, all of (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/355,246
(22) PCT Filed: Jan. 30, 1998
(86) PCT No.: PCT/FR98/00182
§ 371 Date: Sep. 17, 1999
§ 102(e) Date: Sep. 17, 1999
(87) PCT Pub. No.: WO98/34116
PCT Pub. Date: Aug. 6, 1998

(30) Foreign Application Priority Data

Jan. 30, 1997 (FR) .............................. 97 01313

(51) Int. Cl.[7] .......................................... G01N 33/553
(52) U.S. Cl. .................. 436/518; 436/523; 436/524; 436/526; 436/528; 436/532; 436/533; 436/534; 436/536; 436/538; 436/540; 436/541; 436/164; 436/173; 436/801; 436/805; 436/806; 436/807; 436/824; 435/7.1; 435/7.2; 435/7.92; 435/7.93; 435/7.94; 435/7.95
(58) Field of Search .................. 436/518, 523, 436/524, 526, 528, 532, 533, 534, 536, 538, 540, 541, 164, 173, 801, 805, 806, 807, 824; 435/7.1, 7.2, 7.92–7.95

(56) References Cited

U.S. PATENT DOCUMENTS

| | | |
|---|---|---|
| 4,018,886 A | 4/1977 | Giaever |
| 4,230,685 A | 10/1980 | Senyei et al. |
| 4,297,337 A | 10/1981 | Mansfield et al. |

(List continued on next page.)

FOREIGN PATENT DOCUMENTS

| | | |
|---|---|---|
| EP | B1 0 106 873 | 5/1984 |
| EP | A2 0 317 286 | 5/1989 |
| EP | A1 0 419 367 | 3/1991 |

(List continued on next page.)

OTHER PUBLICATIONS

A. Risoen et al., One–Step Magnetic Purification of Recombinant DNA–Binding Proteins Using Magnetizable Phosphocellulose, Protein Expression and Purification 6, pp. 272–327 (1995).

B. Hirschbein et al., Magnetic Separations in Chemistry and Biochemistry, Chemtech, pp. 172–179, (1982).

B. Gladbach, *Mini Macs—The New Attraction in Cell Separation Technology*. Date: Unknown.

A. Kumar et al., Patterning Self–Assembled Monolayers: Applications in Materials Science. Langmuir 10, pp. 1498–1511 (1994).

*Primary Examiner*—Long V. Le
*Assistant Examiner*—Pensee T. Do

(57) ABSTRACT

The present invention relates to a method for at least one of detecting, quantifying or isolating at least one analyte from a liquid medium in which the analyte is distributed and comprises providing a reagent comprised of particles having a receptor for an analyte fixed to the particles distributed in the medium and a capturing means having an exposed surface defining an active zone. An intermediate reagent is formed by the complex of the reagent with the analyte. A second receptor is fixed in the active zone to capture either the analyte bound by the reagent or the receptor (capture partners). The active zone serves as a site of isolation and concentration of the capture partners.

22 Claims, 11 Drawing Sheets

U.S. PATENT DOCUMENTS

| | | | |
|---|---|---|---|
| 4,375,407 A | * 3/1983 | Kronick | |
| 4,452,773 A | * 6/1984 | Molday | |
| 4,795,698 A | 1/1989 | Owen et al. | |
| 5,071,774 A | * 12/1991 | Vorpahl et al. | 436/501 |
| 5,169,754 A | 12/1992 | Siiman et al. | |
| 5,186,827 A | 2/1993 | Liberti et al. | |
| 5,318,914 A | * 6/1994 | Matte et al. | 436/526 |
| 5,356,713 A | 10/1994 | Charmot et al. | |
| 5,510,084 A | * 4/1996 | Cros et al. | 422/104 |
| 5,543,289 A | 8/1996 | Miltenyi | |
| 5,646,001 A | * 7/1997 | Terstappen et al. | 435/7.21 |
| 5,655,665 A | 8/1997 | Allen et al. | |
| 5,660,990 A | * 8/1997 | Rao et al. | 435/6 |
| 5,695,936 A | * 12/1997 | Mandrand et al. | 435/6 |
| 5,698,271 A | * 12/1997 | Liberti et al. | 427/550 |
| 5,723,344 A | * 3/1998 | Mabilet et al. | 436/518 |
| 5,773,307 A | * 6/1998 | Colin et al. | 436/526 |
| 5,902,746 A | * 5/1999 | Colin et al. | 435/306.1 |
| 5,925,573 A | * 7/1999 | Colin et al. | 436/525 |
| 6,120,856 A | * 9/2000 | Liberti et al. | 427/550 |

FOREIGN PATENT DOCUMENTS

| | | | |
|---|---|---|---|
| EP | A1 0 528 708 | | 2/1993 |
| EP | A2 0 585 868 | | 3/1994 |
| EP | A2 0 125 995 | | 11/1994 |
| WO | WO 88/00060 | | 1/1988 |
| WO | WO 90/07380 | | 7/1990 |
| WO | WO 96/09409 | * | 3/1996 |
| WO | WO 96/26011 | | 8/1996 |
| WO | WO 96/26782 | | 9/1996 |
| WO | WO 97/07243 | * | 2/1997 |

\* cited by examiner

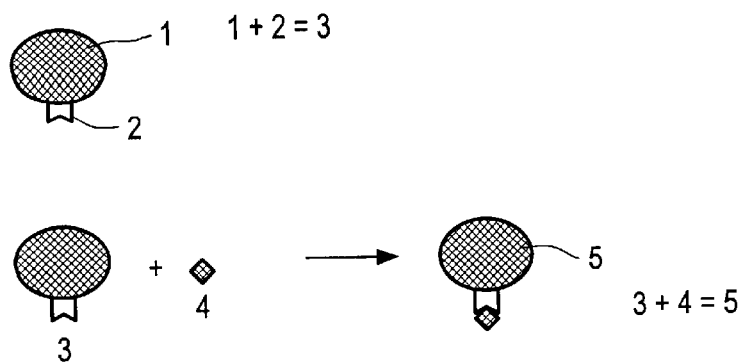
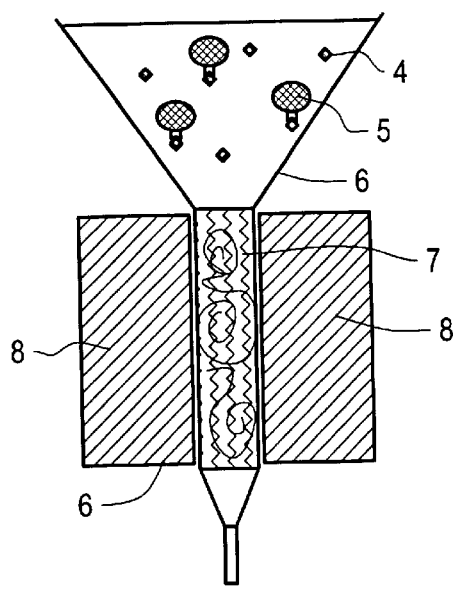
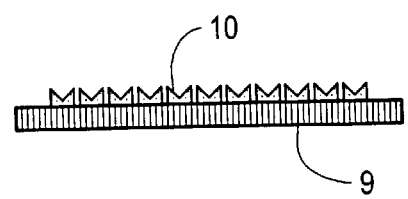
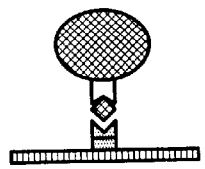
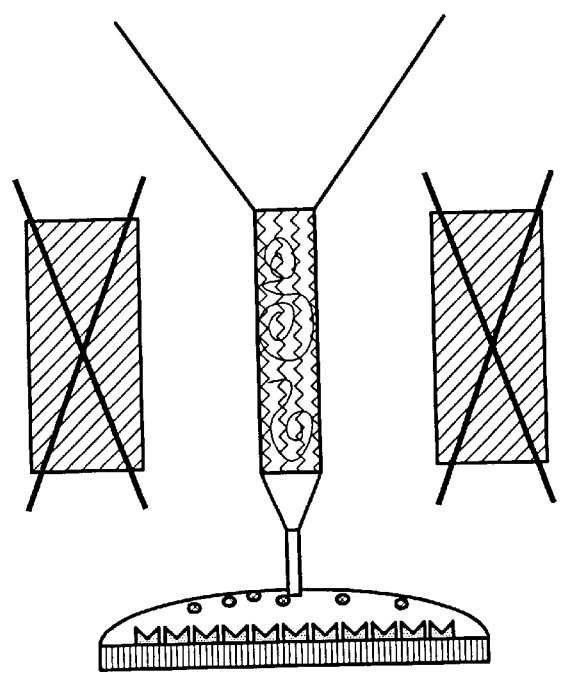

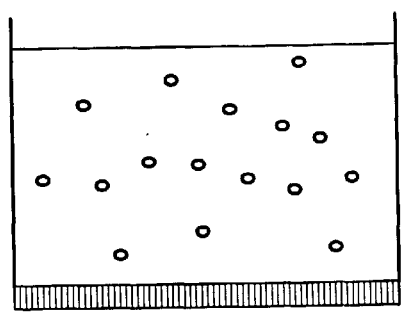 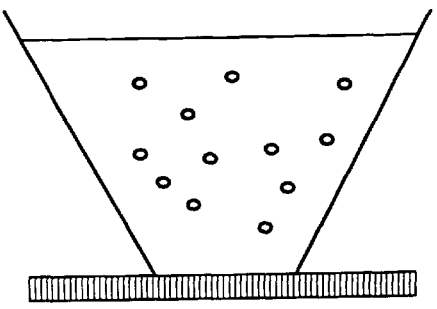
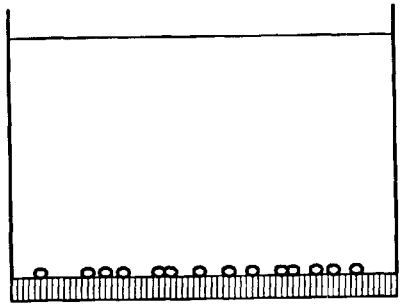 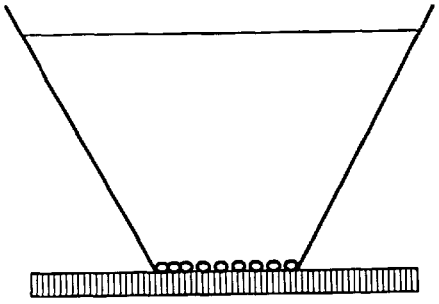
FIG 6A                    FIG 6B
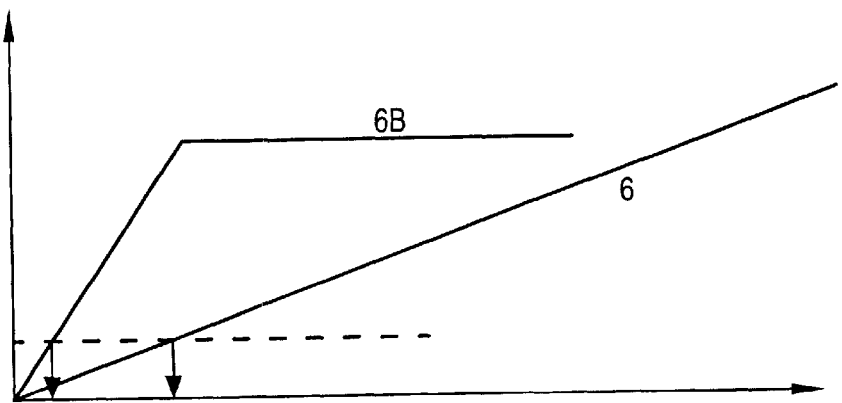
FIG 7

METHOD FOR ISOLATING, IN PARTICULAR FOR DETECTING OR QUANTIFYING AN ANALYTE IN A MEDIUM

BACKGROUND

The present invention relates to a method for isolating at least one analyte from a liquid medium, in which the latter is distributed.

"Isolating" or "isolation" is generically understood to mean any technique which makes it possible to separate said analyte, but also to enrich or concentrate, in relation to said analyte, any liquid mixture containing it. However, it is also understood to mean, optionally conjointly with the preceding definition, any technique which makes it possible to determine the analyte, for the purpose of a detection and/or quantification thereof, in the liquid medium containing it.

"Analyte" is understood to mean any entity, in particular biological entity, to be isolated. Among the range of the analytes considered below by the present invention, there may be mentioned cells, organelles, viruses and bacteria, antibodies, antibody fragments, antigens, haptens, lectins, sugars, ribodeoxyribo-nucleic acids, proteins, in particular A or G, hormones, hormone receptors, biotin, avidin, streptavidin and in general all natural or synthetic molecules or macromolecules, or analogs, to be determined, that is to say detected and/or quantified.

In accordance with the document FR-A-2,679,660, a method is known for isolating at least one analyte, namely either an antigen which is free or bound to the surface of a cell, or an antibody directed against a cellular or tissue antigen, for example anti-erythrocyte antibody.

According to this method, at least one reagent is available which comprises, on the one hand, a free support, in discrete form, in this case relatively large-sized magnetic particles consisting of a polymer which encapsulates ferrite granules, and, on the other hand, exhibiting a receptor for the analyte, namely either an antibody, or an antigen or revealing substance, for example an anti-human immunoglobulin antibody.

Another support, for capture, is also available which consists of the wall of a container or well, whose accessible surface comprises at least one useful or active zone, of limited surface, exhibiting at least one other receptor for an entity to be captured, namely for said analyte or for said receptor. This other receptor is either an antibody, or an antigen, for example of the erythrocyte type.

According to this method, the accessible surface of said other support is brought into contact with the analyte, contained in a liquid sample, in order to bind the analyte to the accessible surface, and to assemble it in the form of a deposit on said surface, immobilized on said other support via said other receptor.

Next, for revealing purposes, the reagent is brought into contact with the immobilized analyte, in order to obtain with the latter a combination, also immobilized on said other support and capable of allowing the isolation or determination of the analyte.

A method as defined above is therefore carried out with a reagent consisting of a support in discrete form, to which at least one ligand forming a receptor for the analyte is bound.

Preferably, these particles are magnetic. They can be classified into two categories, namely particles of relatively large diameter, for example of the order of one or a few micron(s), and those of relatively small diameter, for example of the order of a few tens of nanometers, and in the colloidal state.

The magnetic particles of relatively large diameter, when they are placed in a magnetic field, move in the direction of the site where the field is highest and at a sufficient speed to be separated from their medium by this means.

By way of example, there may be mentioned the particles described in the document EP-A-0,125,995. They are obtained by precipitation of ferrous and ferric salts in basic medium, followed by a silanization reaction in methanol. Their final diameter is between 0.1 and 1.5 $\mu$m and their density is 2.5 g/cm$^3$. Likewise, the particles described in the documents EP-A-0,106,873, EP-A-0,585,868 and U.S. Pat. No. 5,356,713 are obtained by various methods of polymerization, or alternatively those described in the document U.S. Pat. No. 4,297,337 use a porous glass matrix in which magnetic pigments are dispersed. Other patents also describe the use of small-sized particles, but deliberately aggregated in order to increase the magnetic mass as in the document U.S. Pat. No. 5,169,754. The article by P. A. Risøen et al, Protein Expression and Purification, 6 (1995), 272–277 also describes magnetic gels.

Placed in a magnetic field, all these relatively large particles generate a movement in the direction of the side where the field is the most intense. A simple permanent magnet or equivalent assemblies as described for example in the document EP-A-0,317,286 or U.S. Pat. No. 565,665 may be used. These particles are commonly used for the separation of cells or of molecules, as well as in immunoassays as described in the document EP-A-0,528,708 but are not used as systems for detection and quantification.

Moreover, their diameter and their density are such that they sediment very rapidly under the effect of gravity, which makes them difficult to use because of the stirring stresses or lack of homogeneity of the solutions due to the creation of a concentration gradient.

In summary, the relatively large particles are difficult to use and are not very appropriate for the determination of an analyte.

Magnetic particles of relatively small diameter are practically not attracted by a simple permanent magnet within reasonable periods: these particles are in particular widely used for the magnetic separation of cells. These particles are known to persons skilled in the art by the name of "superparamagnetic" particles. "Superparamagnetic" particles are understood to mean particles whose diameter is too small to consist of several magnetic domains. They are characterized by a high magnetic susceptibility and a high magnetization at saturation, but a zero or very low magnetic stability. These particles are in particular widely used for the magnetic separation of cells. For example, those described in the document U.S. Pat. No. 4,230,685 are obtained by emulsifying a mixture of albumin, of protein A and of particles of Fe$_3$O$_4$ 15–20 nm in diameter and can immobilize antibodies via the protein A. The document U.S. Pat. No. 4,452,773 describes another type of particle, obtained by precipitation of ferrous and ferric salts in a basic medium, and in the presence of a polysaccharide. These particles can immobilize antibodies, oligonucleotides, lectins or other biomolecules, by coupling to the polysaccharide by means of known methods of grafting. Their use has often been repeated, as in the documents U.S. Pat. No. 5,543,289 or WO-A-88/00060, or they are used in specific applications such as those described in the documents FR-A-2,710,410 and FR-A-2,732,116. The document U.S. Pat. No. 4,795,698 describes a modification of the Molday procedure, by replacing, for example, the polysaccharide with another polymer of a protein nature. The proteins present at the surface of the particles can thus serve for the subsequent immobilization of antibodies by coupling methods known to persons skilled in the art.

These particles require the use of special assemblies which make it possible to locally increase the magnetic field gradient. This technique is known by persons skilled in the art by the name of HGMS (for High Gradient Magnetic Separation) and it is for example described by WO 96/09409. It uses a device discrete form and for this reason are not used for the separation, concentration or enrichment of an analyte.

Furthermore, after separation, the particles are rather considered as an inconvenience in the subsequent steps of any method. In the document U.S. Pat. No. 4,018,886, they are even removed deliberately. The document FR-A-2,710,410 uses the presence of small-sized superparamagnetic particles as detection components which make it possible to quantify a molecular recognition reaction. In this case, the principle used is an agglutination reaction resulting in the formation of an aggregate. Furthermore, the articles are not used as a means of concentrating or of separating the component to be separated, but solely as a means of detection.

In summary, relatively small magnetic particles are not very appropriate for separation, enrichment or concentration procedures, in traditional procedures, in particular immunoassays.

The document WO-A-96/09409 describes the use of the so-called MACS (Magnetic Cell Sorting) method, involving the formation of a complex between an analyte and a reagent comprising magnetic particles, for enriching/concentrating said analyte, in this instance fetal erythrocytes. These cells are then analyzed by flow cytometry, or used as a source of genetic material, but without being immobilized on a support, through bonding between the analyte and a receptor for example.

The document DE-A-4,036,288 describes a method which makes it possible to detect and quantify one or more analytes specifically bound to particles which are capable of being distinguished.

The subject of the present invention is a method, which makes it possible to isolate an analyte from a liquid medium in which it is extremely dilute or not concentrated to any great extent. More particularly, as regards the determination of the analyte, the subject of the present invention is a method allowing a high sensitivity of detection and/or of quantification.

In accordance with the present invention, in general:
the reagent is brought into contact with a liquid sample obtained from the medium containing the analyte, to form an intermediate medium comprising, still in a discrete form and distributed in said medium, a complex between said support, the receptor and the analyte,
the accessible surface of said other support is brought into contact with at least one capture partner,
The deposit of the capture partner is concentrated by obtaining, from the intermediate medium, another sample, enriched with capture partner; and said other sample is brought into contact with the accessible surface.

A liquid stream, containing the capture partner, of limited section and adapted to the accessible surface, is established and said stream is brought into contact with said accessible surface.

A liquid stream, containing the capture partner, is established and said stream is brought into contact with said accessible surface, and then recycled in contact with the latter.

Before the description of the invention, it is appropriate to give a definition of the terms used.

"Ligand" is understood to mean a component capable of forming, through a chemical or physical bond, a complex with an analyte.

By way of example of ligand, there may be mentioned antibodies, antibody fragments, antigens, haptens, lectins, sugars, ribo- and deoxyribonucleic acids, proteins, in particular A or G, hormones, hormone receptors, biotin, avidin or strepta-,idin and, in general, it being possible for natural or synthetic ligands, and modified ligand analogues to enter into competition with the ligands.

"Receptor" is understood to mean any ligand as defined above, immobilized on a support by any means such as adsorption, covalent bonding, chelation, molecular recognition, and the like, and capable of retaining an analyte, alone or conjugated with another ligand.

"Support" is understood to mean any type of support, polymeric, inorganic or metallic. By way of example of polymeric supports, there may be mentioned plastic supports based on polystyrene, poly(meth)-acrylates, polybutadiene, polypropylene, and the like, alone or in the form of copolymers. By way of example of inorganic supports, there may be mentioned silicon oxide, silicon, mica, glass, quartz, and the like. By way of example of metallic supports, there may be mentioned gold, silver, titanium oxide, vanadium oxide, and the like.

The immobilization of the ligands on the support may be carried out either by simple adsorption on the native or modified support, or via a chemical or physical reaction which makes it possible to modify the surface of the support, and thus to allow the binding of the receptor by covalent bonds, or other traditional means well known to persons skilled in the art.

"Limited surface" is understood to mean any surface obtained by chemical or physical means, designed to reduce a surface of defined dimensions, for example by cutting into smaller-sized components, by covering with a "mask" which limits the initial surface to the inner contours of the mask, or by chemical means of spreading based on a smaller surface, as described in Kumar A. et al. (Langmuir (1994), 10, 1498–1511). The reduction in the surface of the useful or active zone is not limited in size. Methods derived from microtechnologies make it possible, for example, to obtain limited surfaces of micro or nanoscopic sizes, as well as to have available and/or to convey micro or nanovolumes of liquids to said useful zone of limited surface.

In the description below, the term "conjugated" will be reserved for the entity formed by immobilization between the ligand and the support of the reagent. The term "complex" will be reserved for the entity formed between the reagent, hypothetically conjugated, and the analyte. Whether it is the support which is part of the reagent, the reagent itself, and the complex, they are in a discrete form, distributed or dispersed in a liquid medium, and consequently in the form of particles.

The terms "support" and "other support" indicate that they are components which are substantially of the same nature or having essentially the same function. The term "support" will be reserved for the support belonging to the reagent, and the term "other support", to the support of which at least part of the accessible surface or window contains one or more useful zones of limited surface.

The terms "receptor" and "other receptor" will be reserved respectively for the ligands immobilized respectively on said support and said other support.

"Particle" is understood to mean any particle of a polymeric, inorganic or metallic support, on which it is possible to graft a ligand. In particular, the particles which may be separated by the action of an external physical means, for example by a magnetic or electrical route, or under the effect of gravity or by centrifugation are considered as falling within the scope of the present invention. Falling outside the preceding definition are the small-sized, in particular superparamagnetic, particles whose speed of sedimentation under the effect of gravity is less than the thermal agitation, but which are capable of constituting aggregates by any method which makes it possible to combine them with each other, or to assemble them on larger-sized particles, which can be separated by any physical means.

By way of example of polymeric particles, there may be mentioned the particles obtained by polymerization in emulsion such as latexes or larger-sized particles, magnetic or otherwise.

By way of example of metallic particles, there may be mentioned colloidal gold, ferro-, ferri-, para-or superparamagnetic particles, coated or otherwise with natural or synthetic polymers, whose composition comprises iron or other metals such as cobalt, nickel, alone or in the form of alloys, magnetic or otherwise.

By way of example of inorganic particles, there may be mentioned particles based on silica or silicon, magnetic or otherwise.

By way of example of methods of separation by an external physical means, there may be mentioned sedimentation by gravity or by centrifugation, magnetic attraction by the action of permanent magnets, of electromagnets, or by the use of devices which make it possible to increase the magnetic field gradient, the electrical attraction, and any other equivalent technique.

"Determination" is understood to mean any method which makes it possible to detect the presence and/or to quantify the deposit concentrated in the useful zone of the accessible surface of said other support, namely the particles of the specific product of interest, that is to say of the complex or the reagent which has not reacted.

By way of example of a method of determination, there may be mentioned:

topographical methods such as atomic force microscopy, profilometry, and the like, magnetic methods as described, for example, in the document FR-A-2,710,410, magnetic force microscopy, and any methods of determination which are sensitive to the presence of ferro, ferri, para and super paramagnetic metallic components electrical methods such as the measurement of a variation in capacitance, described for example in the document EP-A-90 402 611, tunnelling microscopy, impedance measurements, and the like optical methods which allow the detection, for example, of a modification of the thickness and/or of the refractive index (optical thin layers, ellipsometry, surface plasmon resonance, surface acoustic waves, and the like) or the measurement of a light intensity (evanescent waves, dark field microscopy, optical near field microscopy, and the like)

methods which allow the measurement of mass variations (quartz crystal microbalance, and the like)

and in general, any techniques not cited here, but which are equivalent.

The present invention can accomodate various embodiments, depending on the operating choices defined below.

In the concentration step, the capture partner concentration level is determined so that the quantity of said immobilized capture partner remains at most equal to the quantity of said other receptor on said other support. To this end, for example, the reagent comprises particles of the support conjugated with the receptor, having the capacity to be separated from any liquid medium in which they are dispersed, under the action of a physical means applied to the liquid medium, and this physical means is applied to at least part of the intermediate medium, in order to separate the complex particles, these complex particles thus separated are optionally washed, and the complex particles are recovered, by ending the application of the physical means, in order to subsequently obtain, in said useful zone, a deposit concentrated in relation to the capture partner. By way of example, the particles of the support are magnetic, in particular superparamagnetic, and the physical means consists of a magnetic field applied to the intermediate medium, for example according to the so-called HGMS (High Gradient Magnetic Separation) technique.

The receptor, that is to say the one belonging to the reagent, and said other receptor, that is to say the one for the accessible capture surface, contain the same ligand, immobilized respectively on the support and said other support.

When the reagent comprises particles of the support conjugated with the receptor, having the capacity to be separated from any liquid medium in which they are dispersed, under the action of a physical means applied to this liquid medium, this physical means is preferably applied in relationship with the other support, that is to say the one for capture, in order to concentrate said deposit in any useful zone.

In some cases, the reagent is labeled, and the treatment of the analyte comprises a step of determining the marker for the deposit concentrated, immobilized in the useful zone of the other support, that is to say of the capture support. Conventionally, this labeling of the reagent is obtained according to one of the following modes, namely:

the support itself constitutes a marker; it is for example colloidal gold the marker is bound to the support the marker is bound to the receptor.

The analyte is determined from the deposit concentrated in the useful zone, by any method chosen from the group including topographical methods, for example by atomic force microscopy (AFM), magnetic methods, for example by magnetic force microscopy, electrical methods, for example measurement of a variation in capacitance, optical methods, for example measurement of the refractive index, and finally methods for measuring mass variation, for example quartz crystal microbalance.

More particularly, the useful zone is designed so that the quantity of said deposit immobilized on said other support is at least equal to the sensitivity threshold of the method of determination, expressed as number of particles per unit of surface.

The assay format used is either direct, in which case said capture partner is said analyte, or by competition, in which case said capture partner is said reagent.

Preferably, another sample is obtained, by enriching said intermediate medium with complex, and said other sample is brought into contact with the accessible surface of said other support.

Various modes of bringing the other sample into contact with the accessible capture surface are considered:

a measured quantity of said other sample is deposited on the accessible surface of the latter or a stream of said other sample, of a relatively small thickness, optionally recycled, is caused to pass in contact with this accessible surface.

Finally, the liquid medium may contain a plurality of various analytes, and in this case the accessible capture surface of the other support comprises a plurality of useful zones, exhibiting a plurality of other receptors which are respectively different, of capture partners which are respectively different.

The method according to the invention may be applied to a specific nucleic material of any bacterium, in this instance ribosomal RNA, in which case the sensitivity level obtained makes it possible to avoid any enzymatic amplification method, such as PCR (Polymerase Chain Reaction), applied to the genomic material of the same bacterium, in order to detect the latter. Indeed, the sensitivity level obtained becomes compatible with the quantity of ribosomal RNA present in the bacterium, of the order of $10^4$ to $10^5$ molecules, which makes it possible to determine the presence of this bacterium, without using amplification of all or part of its genome.

DESCRIPTION OF THE FIGURES

FIG. 1 represents a general diagram of the formation of the complex in solution.

FIG. 2 shows an example of a device for separating the complex.

FIG. 3 represents a biospecific, accessible surface of the capture support. FIG. 4 represents the deposition of the solution containing the complex on the biospecific surface. FIG. 5 represents the reaction between the complex and the other receptors of the biospecific surface.

FIG. 4 represents an example of deposition of the solution containing the complexes.

FIG. 5 represents an example of the reaction between the complex and the receptor on the support.

FIGS. 6A and 6B schematically present two methods which make it possible to assemble and immobilize particles of the complex on the biospecific surface, one without concentration of the complex (FIG. 6A), and the other with concentration of the complex (FIG. 6B).

FIG. 7 represents two curves derived from the methods presented in FIGS. 6A and 6B, respectively. The number of particles detected per unit of surface is represented on the y-axis, and the analyte concentration of the original liquid medium on the x-axis. The dotted line establishes the sensitivity threshold.

DETAILED DESCRIPTION OF THE PREFERRED EMBODIMENTS

Figures 8, 9A, 9B:
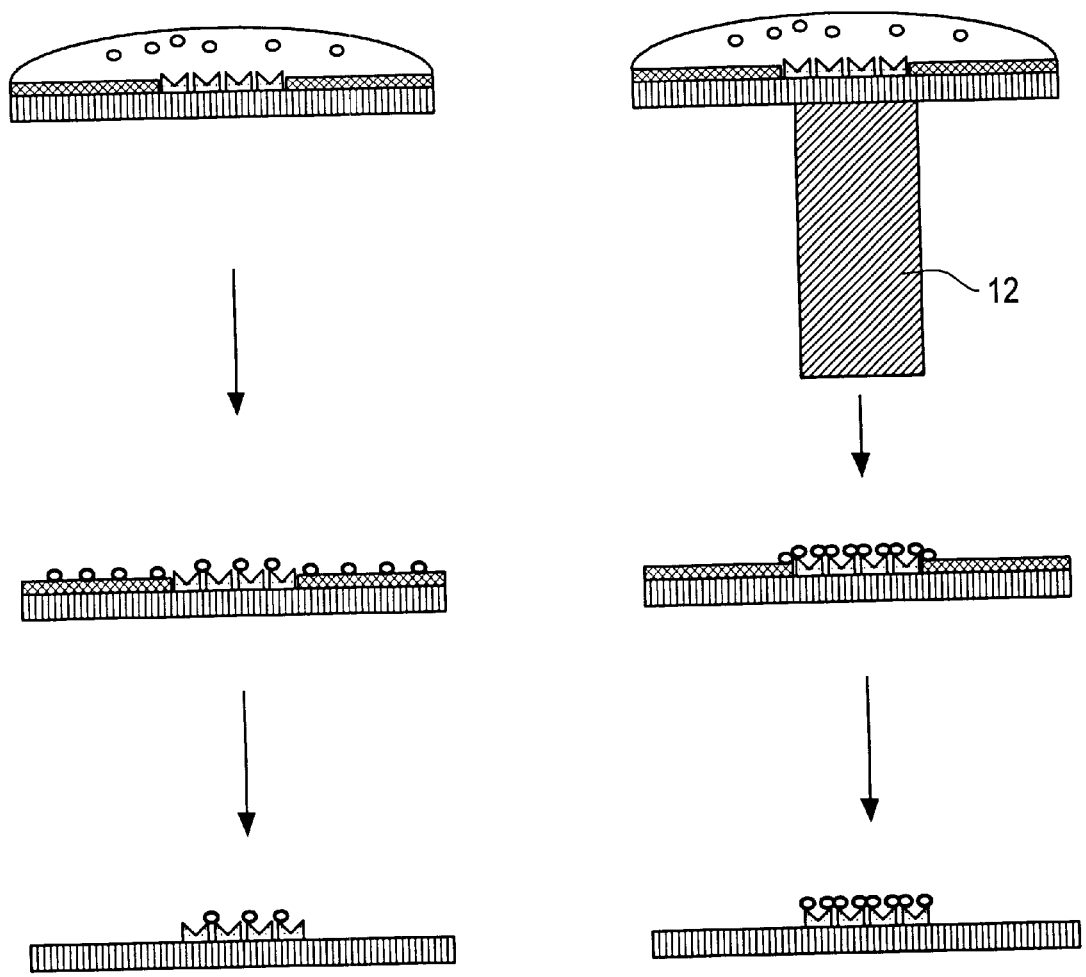
FIG. 8 shows a surface accessible to the complex, belonging to said other support, termed capture support, limited by the use of a mask.
FIGS. 9A and 9B present the deposition of particles of the complex on the limited surface represented in FIG. 8, respectively without and with a means of concentrating, consisting of a magnet or electromagnet.

As previously mentioned, a particular feature of the invention is a method which makes it possible to isolate analytes, even when highly diluted, from liquid media. The mode of isolation may be variable, an example is given as a guide in order to facilitate understanding. This mode has the advantage of using small-sized magnetic particles. FIG. 1 shows an example thereof.

In a specific embodiment, the particles 1 used have a diameter of between 10 and 1000 nm, preferably between 10 and 200 nm. They comprise at least one monocrystalline iron oxide core, having a diameter of between 7 and 15 nm, itself surrounded by a layer of a hydrophilic polymer (support), so as to avoid contact between the metallic core and the ligand forming the receptor. The metallic core, given its size, has a superparamagnetic character. Such suspensions are stable for several months, without notable sedimentation. The polymer may be advantageously used for the immobilization or grafting of the ligands according to methods known to persons skilled in the art. The polymer used here is a polysaccharide called Dextran®, having a molar mass of between 10,000 and 2,000,000, preferably between 40,000 and 70,000. It may be activated or functionalized, as appropriate, by various methods such as oxidation with periodate, giving aldehyde functions by cleavage between vicinal alcohol functions, or with cyanogen bromide, and in general, by any equivalent method.

The ligands 2 are either antibodies, antigens, oligonucleotides or any other biological entity having the property of binding to an analyte, as was defined above. The ligands may, for example, be coupled to the surface of the particles, to the functions of the previously activated polymer, via primary amine functions existing in the native molecule or intentionally added to the ligand. The particle/ligand conjugate 3 is represented in FIG. 1.

FIG. 1 represents a general diagram of the formation of the complexes in solution. The conjugate 3 (reagent) is introduced into the medium containing the analyte 4 to be separated. After an incubation time necessary for the formation of the complex 5 between the conjugate and the analyte, the solution (intermediate medium) is passed over the assembly represented in FIG. 2. This is an example of an enrichment device based on the principle of a separation of components which respond to the influence of a magnetic field. It contains a separating chamber 6 housing a matrix of filaments made of ferromagnetic material, such as steel filaments 7. This matrix maybe coated, as appropriate, with a polymer, as described in the documents U.S. Pat. No. 4,375,407 or WO-A-90/07380. The solution containing the analyte/reagent complexes 5 is passed over the filamentous matrix placed in the magnetic field of one or more magnets 8, at a flow rate which is adjustable and which allows the complex to be retained by the matrix. Such a device makes it possible to enrich the complex diluted in very large initial volumes.

After elimination of the foreign components and of the carrier liquid, the magnetic field is removed, and the concentrated complex is eluted with a small volume of liquid. This volume is deposited on a biospecific, accessible surface represented in FIG. 3. It consists of a flat support 9 on which other receptors 10 specific for the analyte 4 are immobilized.

A flat support such as silicon oxide has known advantages. There may be mentioned, for example, a low roughness, adjustable sizes or varied modes of functionalization. For example, the attachment of alkoxy or of chlorosilanes allows the introduction of functions at the surface, with the aim of immobilizing receptors in various ways (adsorption, covalent bonding, and the like), and the like. Other types of supports as described above can however be used.

FIG. 4 represents an example of deposition of the solution containing the complexes 5. It is eluted by removing the magnetic field and is eluted and deposited on the biospecific surface in a small volume.

FIG. 5 represents an example of the reaction between the complex 5 and the receptor 10 on the support 9.

FIGS. 6A and 6B present one of the advantages of the invention. In FIG. 6A, a given number of particles is concentrated on a so-called wide biospecific surface. FIG. 6B presents an improvement, in that the same number of particles is concentrated on a biospecific surface which is smaller in size than on the assembly in FIG. 6A.

FIG. 7 represents a theoretical curve showing the increase in the number of particles per unit of surface, according to the assemblies represented in FIGS. 6A and 6B. If a sensitivity limit (dotted lines) is represented, it is advantageous to use a reduced surface, in that this allows an improvement in the sensitivity threshold and therefore the detection of lower concentrations of particles solution.

FIG. 8 shows an exemplary embodiment intended to limit the biospecific surface constituted by a single useful capture zone. It is identical to the biospecific surface represented in FIG. 4, but its size has been limited by the use of a mask 11 of controlled size.

In accordance with the preceding description, FIGS. 9A and 9B present a specific carrying out of the deposition of particles on the reduced surface represented in FIG. 8. FIG. 9B presents another advantage of the invention. It is an improvement of the mode represented in FIG. 9A, by the addition of a magnet 12 placed under the support and intended to concentrate the complexes 5 on the usefuli zone 10.

Figure 10:
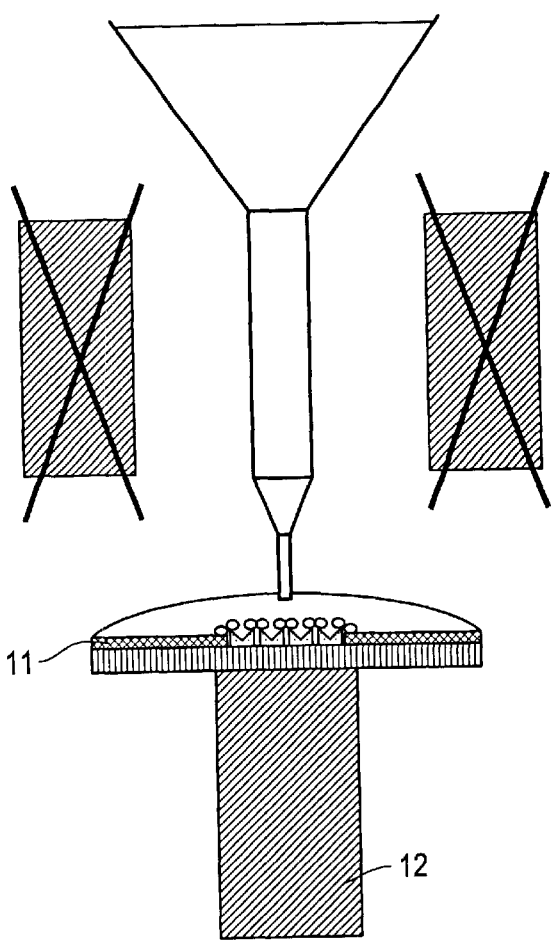
FIG. 10 represents a system identical to that represented in FIG. 4, with the limited surface represented in FIG. 8 and the addition of a magnet.
Figure 11:
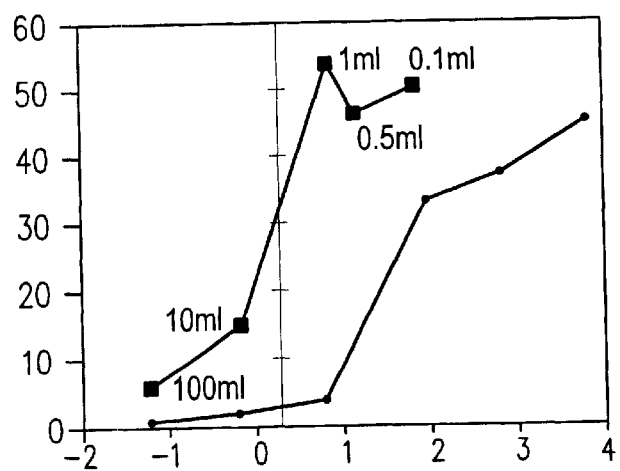
FIG. 11 represents the effect of enriching with complex by a magnetic field gradient, on the variation in the number of particles per unit of surface ($\mu m^2$) on the y-axis, as a function of the TSH (analyte) concentration on the x-axis [Log10 ng/ml]. The black circles refer to an absence of enrichment with a constant volume of 0.07 ml, the black squares to a variable volume concentrated by HGMS.

FIG. 10 represents a system identical to that represented in FIG. 4, with the two refinements of the invention described above: the reduction in the accessible surface by the addition of a mask 11, and the concentration or confinement of the particles on a surface of reduced size by the addition of a magnet 12.

Figure 24:
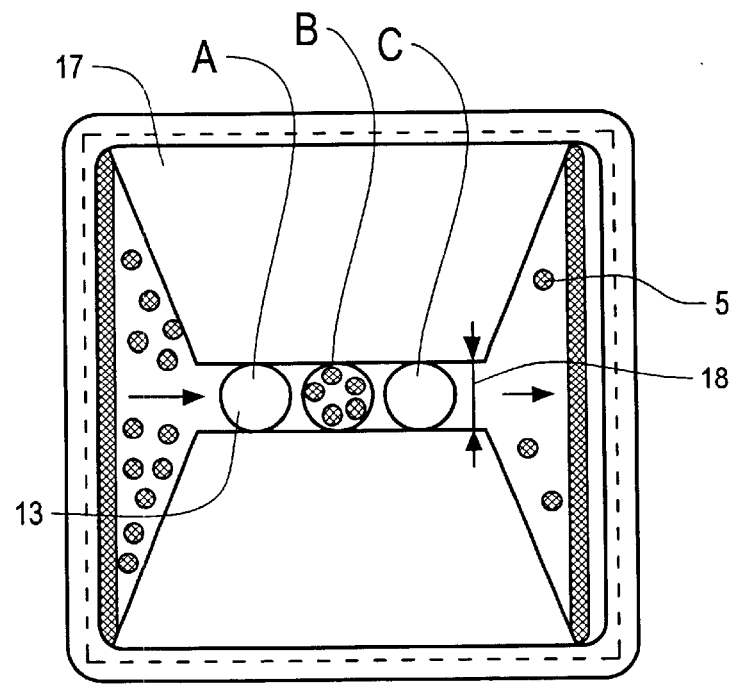
Figure 25:
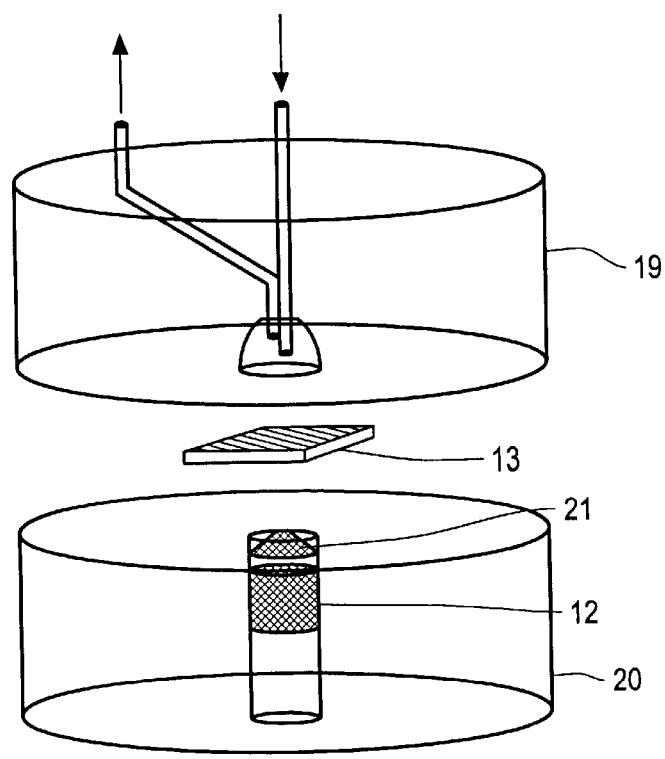
FIGS. 25 and 26 represent another embodiment of the invention. They present in particular the addition, to the surface of the magnet, of a pointed parted part made of a so-called "soft" magnetic material having the propert of confining the magnet field line to the end of this tip. This part or the equivalent can equally well be added to the examples described in FIGS. 9B, 10, 18, 21, 23 and 24 or any other equivalent assembly.
Figure 26:
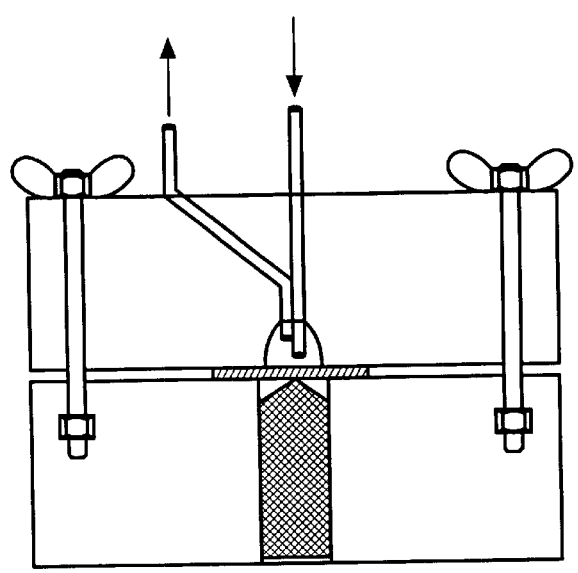

FIG. 25 and represent another embodiment of the invention. They present in particular, in the lower part 20, the addition, to the surface of the magnet, of a pointed part of a so-called "soft" magnetic material having the property of driving and confining the magnet field lines to the end of this tip. This part or the equivalent may equally well be added to the embodiments according to the examples described in FIGS. 9B, 10, 18, 21, 23 and 24, or any other equivalent assembly. The upper part 19 is provided with an inlet and with an outlet allowing the analytes 4 or the complexes 5 in the sample to be brought into contact with the receptors 10 of the capture surface 13.

Additional details relating to the carrying out of the invention are indicated in the following examples.

EXAMPLES

Example 1

Manufacture of Biospecific, Limited Surfaces by Coupling Anti-TSE (Thyroid Stimulating Hormone, or Analyte) Antibodies The support used is composed of 8×8 mm silicon plates, coated with thermal silica. Possible organic contaminants are first removed by cleaning in the sulfochromic mixture. The plates are then immersed in 1 ml of a 2% aminopropyldimethylethoxysilane solution (v/v) in toluene. The amine functions thus created on the surface are activated with 1 ml of disuccinimidyl suberate solution (10 mM in dimethyl sulfoxide).

The capture anti-TSH antibodies are diluted to 40 µg/ml in 50 mM phosphate buffer containing 0.15 M NaCl, pH 7.4 (PBS). 70 µl are deposited on the activated plates. The coupling takes place for 1 hour at room temperature. The plates are then incubated for 2 hours at 37° C. with 70 µl of a solution of albumin at 0.1 mg/ml in PBS buffer containing 0.5% Tween 20® (PBS/Tween), so as to avoid the adsorption of undesirable molecules.

Example 2

Synthesis of the Magnetic Particles (free support)

This synthesis is described in the document U.S. Pat. No. 4,452,773 (Molday), except for a few modifications.

14 grams of polysaccharide Dextran® T40 (Mw=40,000, Pharmacia) are added to 14 ml of water, and the Dextran is left to dissolve at room temperature (solution 1). A solution 2 is prepared with 3 grams of $FeCl_3.6H_2O$ (Mw=270.3) and 1.3 grams of $FeCl_2.4H_2O$ (Mw=198.81) in 20 ml of water. Both solutions are introduced into a 250-ml jacketed reactor equipped with a stirring motor set at 200–250 revolutions/min, a glass stirrer and a dropping funnel containing a 7.5% $NH_4OH$ solution (v/v). At room temperature, the $NH_4OH$ solution is added dropwise, with stirring, until a final pH of between 10 and 11 has been obtained. The temperature is brought to 70° C. for about 60 minutes, and then the final solution is extensively dialysed against 5 liters of distilled water, with renewal of the dialysis baths until a neutral pH has been obtained. The solution is then filtered on quartz wool in order to remove the largest aggregates, and then centrifuged 3 times at 600 revolutions/min for 5 minutes. In order to remove excess Dextran, the particles are deposited on a (33×2.5) cm Sephacryl S300 HR gel column (Pharmacia), previously equilibrated in 0.1 M acetate buffer containing 0.15 m NaCl, 0.05% $NaH_3$, pH=6.5. The superparamagnetic particles obtained, coated with Dextran, have an outer diameter of between 20 and 900 nm, and preferably of between 30 and 100 nm. They are stored at +4° C.

The assay of the particles is carried out by measuring the optical density at 483 nm. A calibration straight line iron(II) salt of known molarity. The percentage by weight of iron in the particles is about 50 (±10) %.

The assay of the Dextran is carried out by the technique described by Molday, R.S. et al (FEBS Lett., 170/2:232, 1973). The optical density of the complexes formed between the polysaccharide and the phenolsulfuric acid mixture is measured at 487 nm. The calibration curve is plotted on free Dextran. The percentage by weight of Dextran in the particles is about 50 (±10) %.

Example 3

Manufacture of Particle/Anti-TSH Antibody Conjugates, in Order to Obtain the Reagent 3.1) Direct coupling of the anti-TSH antibodies to the particles of Example 2

The particles are dialyzed in acetate buffer (0.1 M $CH_3COONa$, 0.15 M NaCl, pH=6.5). 5 µl/mg of particles in a 0.1 M sodium periodate solution in the acetate buffer are added, and the reaction time is 45 minutes, protected from light. The particles thus oxidized are dialyzed in the coupling buffer (0.25 M phosphate, 0.75 M NaCl), and the anti-TSH antibodies are added (10 to 100 µg/mg of particles). The coupling takes place overnight at 37° C. with stirring.

The imine bond is then reduced by addition of sodium borohydride (0.1 M, 1 µmol/mg of particles) for 15 to 30 minutes at room temperature, with stirring. The mixture is finally dialyzed against a 0.1 M phosphate buffer containing 0.15 M NaCl at pH 7.4.

3.2) Use of commercially available particles coupled to streptavidin 3.2.1) Biotinylation of the anti-TSH antibodies:

2 mg of anti-TSH antibodies are dialyzed in PBS buffer, and then brought into contact for 1 hour with biotin-NSH (Pierce), with stirring, at room temperature (20 mol of biotin/mol of antibody). The biotinylated antibodies are again dialyzed in order to remove the excess of biotin.

Example 4

Bringing of the Reagent into Contact with the Analyt, and Enrichment of the Intermeiate Medium Obtained $1.6 \times 10^{10}$ particles of conjugates as obtained in Example 3 are diluted in PBS/Tween® in variable volumes (from 0.1 to 100 ml). 6 ng of TSH are added to each solution and the assays are incubated f or 2 hours at 37° C., with stirring. Each solution is then deposited and enriched on the column described in Example 3, and then washed with 1 ml of PBS/Tween in order to remove the free antigens. To recover the particles, the column is removed from the magnet. 30 µl of PBS/Tween are deposited and removed, because their concentration in terms of particles is too low. 70 µl are then deposited and collected.

Each sample of 70 µl is then deposited on a plate as obtained in Example 1. The solution is left to incubate for 1 hour at room temperature. The plates are then vigorously washed with PBS/Tween, and then with water.

By way of comparison, assays are carried out with solutions of constant volume (70 µl) in which there are mixed, as before, $1.6 \times 10^{10}$ particles of conjugate (reagent) and variable masses of TSH so as to obtain a range of concentrations comparable to those described above (from 0.06 to 86 ng/ml). The solutions are not enriched on a column according to the HGMS technique, but directly deposited on the plates as obtained in Example 1, and incubated under the same conditions as those described above.

Figure 12:
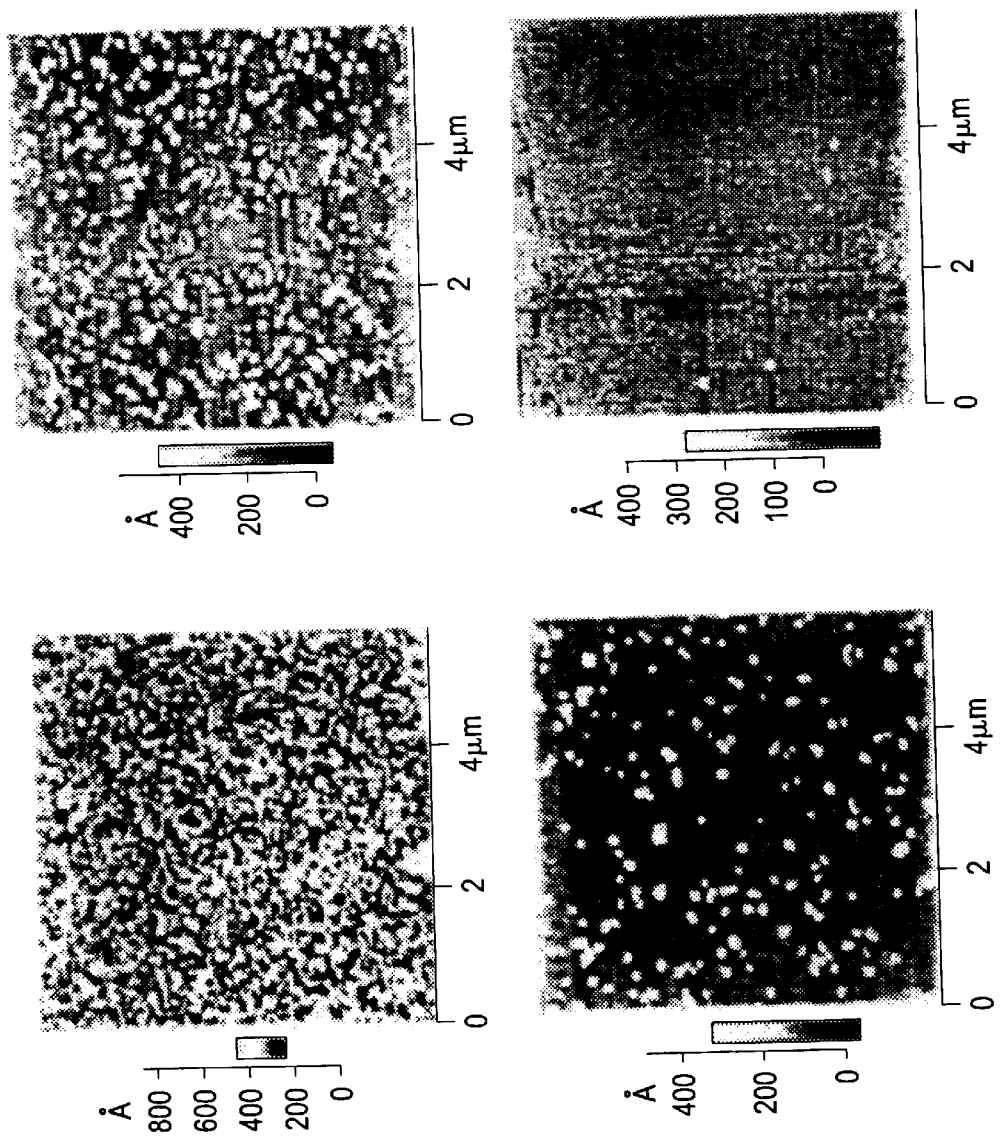
FIG. 12 shows four atomic force microscopy images which represent the effect of the addition of a magnet during the reaction for the formation of conjugates between complexes and receptors of the biospecific or accessible surface of the capture support. The figures on the left are obtained with concentration by a magnet, and the figures on the right without concentration.

The detection of the concentrated deposit of the superparamagnetic complex particles, after specific reaction on the support, is carried out by atomic force microscopy or AFM (Autoprobe, Park Scientific Instrument). The samples are dried with nitrogen, and analyzed in Two of the four plates are placed on a magnet consisting of rare earths (diameter 6 mm, height 25 mm, B=0.32 Tesla), the other two are outside the action of any magnetic field. 70 µl of solutions containing a TSH concentration of 1 or of 100 ng/ml and an identical concentration of conjugated particles ($2 \times 10^9$) are deposited on these plates. The solutions are left to incubate for 1 hour at room temperature, with stirring, so as to limit the nonspecific adsorption of the conjugated particles. The plates are then analyzed by AFM according to the principle described in Example 4, and the results are illustrated by the images in FIG. 12. Although, in this specific embodiment, small-sized magnetic particles are used, the small volumes used allow, all the same, their separation by a permanent magnet because the separation distances are small.

The two plates placed on the magnets show a density of particles which is markedly greater than those for the plates not subjected to the influence of the magnetic field. It was demonstrated that the background noise (absence of TSH in solution) is comparable in both cases, and therefore that the improvement in the antibody/antigen reaction on the biospecific surface is attributable to the presence of the magnet. The results are presented in Table 1.

TABLE 1

| TSH concentration (ng/ml) | Number of particles/$\mu m^2$ (without magnet) | Number of particles/$\mu m^2$ (with magnet) |
|---|---|---|
| 1 | 0.3 | 8.0 |
| 100 | 33 | 128 |

Example 6

Enrichment of the Intermediate Medium on an HGMS Column, and then Application of a Magnet in Relationship With the Biospecific Limited Surface: Influence of the Size of the Biospecific Surface The capture antibodies or ligands are coupled with the activated silica on surfaces of increasing size. For this purpose, variable volumes of 1, 10 and 70 $\mu l$ of antibody solution are deposited at the center of the plates and cover surfaces of 1.8, 13 and 56 mm$^2$, respectively. The smallest surface (0.5 mm$^2$) is made using a punched screen, placed at the center of the plate. The solutions of conjugated particles ($7.6\times10^9$) and of TSH (60 pg/ml) are incubated in 1 ml, and then purified on an HGMS column according to the protocol described in Example 4. The plates as obtained in Example 1 are then placed on the magnets, and the purified solutions are deposited and left to incubate. Analysis by AFM allows the quantification of the number of particles per $\mu m^2$.

Figure 13:
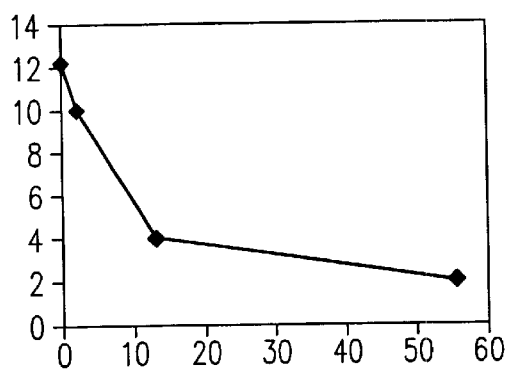
FIG. 13 shows the variation in the number of immobilized particles of the complex per unit of surface ($\mu m^2$), as a function of the size of the biospecific surface in $mm^2$ (on the x-axis).

The results are described in FIG. 13. The number of complex particles immobilized per unit of surface increases when the biospecific surface decreases, and therefore when the complex particles are concentrated at the center of the surface under the influence of the magnet. The smaller the surface on which the complex particles can react, the greater the concentration effect.

Example 7

Enrichment of the Intermediate Medium on an HGNS Column, and then Application of a Magnet in Relationship With the Biospecific, Limited Useful Surface: Influence of the Quantity of Antigen (analyte) in Solution, and Evaluation of the Sensitivity Limit of the Method The capture antibodies or ligands are coupled with activated silica on a surface of 64 or 0.5 mm$^2$. The conjugated particles ($8\times10^9$ per assay) and the antigens (analyte) in variable concentration (from 0 to 500 nglml) are incubated in 1 ml, and then the complex particles are enriched on an HGMS column. The functionalized plates, that is to say coupled to their own receptors, are then placed on magnets as shown in FIGS. 9B and 10, and the purified solutions are incubated, and then analyzed by AFM.

Figure 15:
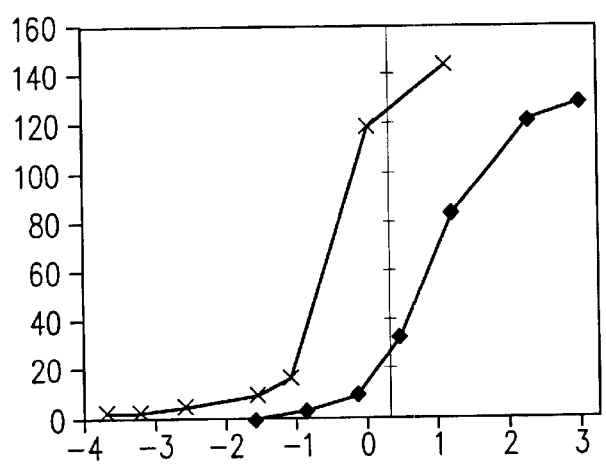
FIG. 15 compares the variation in the number of immobilized particles of the complex per unit of surface ($\mu m^2$), as a function of the original TSH concentration in solution, in ng/ml on the x-axis, according to the size of the biospecific surface. The black circles refer to a complex, first enriched by magnetic field gradient HGMS, immobilized without concentration on a biospecific surface of 64 $mm^2$.The black crosses refer to an enriched complex, immobilized with concentration on a biospecific surface of 0.5 $mm^2$. The concentration on the x-axis is in loglo (ng/ml).

FIG. 15 makes it possible to clearly demonstrate once again the influence of the size of the biospecific useful surface, on the effect of concentration or confinement by magnetization. For the same TSH concentration, a much higher density of complex particles is indeed observed on the small surface (0.5 mm$^2$), represented by crosses, relative to the large surface (64 mm$^2$), for which the density is represented by circles.

Figure 14A:
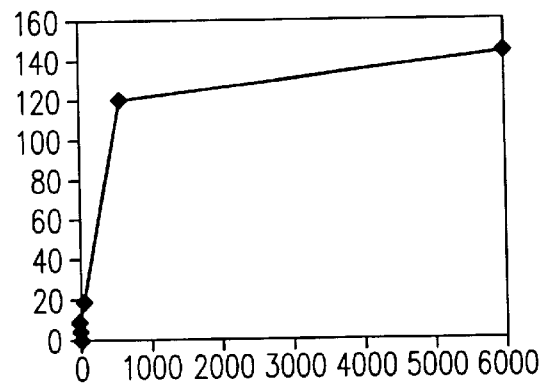
FIG. 14A shows the variation in the number of immobilized particles of the complex per unit of surface ($\mu m^2$), as a function of the original TSH concentration in solution in pg/ml on the x-axis, for a small-sized biospecific surface; the figure on the right (FIG. 14B) shows the original slope.
Figure 14B:
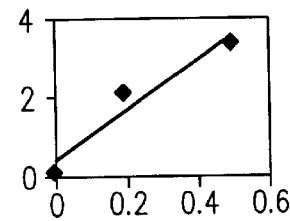

For the concentration on a useful surface of 0.5 mm$^2$, the results are described in FIG. 14. Calculation demonstrates that the value of the plateau obtained is in conformity with the expected theoretical curve (FIG. 7, curve 6B). The limit of detection is calculated as above (Example 6). according to the statistical method generally accepted: 10 blanks (without antigen) are prepared, whose mean roughness ($M_R$) and standard deviation ($SD_R$) are calculated. The limit of detection (LOD) is defined as being: LOD=$M_R$+3. $SD_R$. This value is plotted on the slope at the origin of the calibration curve. A limit of detection of $5\times10^{-3}$ pg/ml, that is to say $1.2\times10^5$ molecules of TSH is calculated (Table 2).

Figure 16:
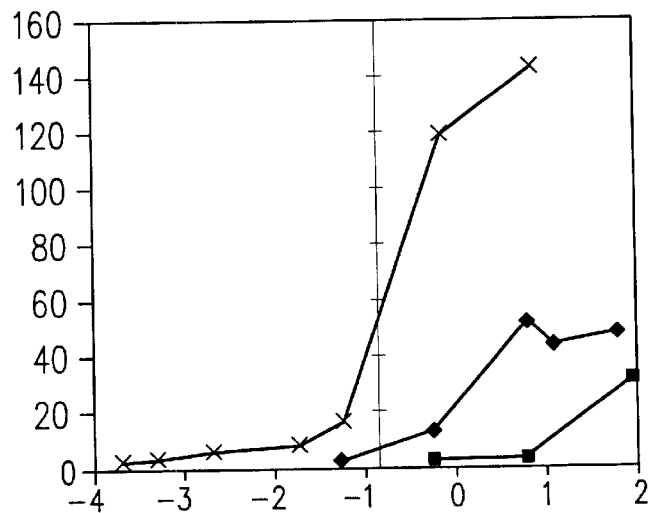
FIG. 16 represents a comparison of the various modes of concentration using magnetic particles for the starting reagent. The y-axis and x-axis are the same, with the same scales, as those represented in FIG. 15. The black circles refer to a complex immobilized on the biospecific surface, without prior enrichment, or concentration at the time of capture on the biospecific surface, the black diamonds to a complex immobilized after enrichment on an HGMS columnn, and the black crosses to a complex immobilized, after enrichment and with concentration.

Comparison of the results:

FIG. 16 presents, on the same graph, the results described in Examples 4 and 7 and makes it possible to demonstrate the improvement in sensitivity provided by the assembly represented in FIG. 10. Table 2 below also makes it possible to show the improvement in the sensitivity limit for the detection of TSH, provided by magnetic enrichment on a column by field gradient on the one hand, and by the joint effect of the magnetic enrichment of the intermediate medium on a column by field gradient and of the magnetic concentration of the complex particles on a small-sized biospecific surface, on the other.

TABLE 2

| Method | Limit of detection (pg/ml) | Useful surface (mm$^2$) |
|---|---|---|
| Column separation by HGMS | 100 | 64 |
| HGMS column separation and concentration by magnetization | 4 | 64 |
| HGMS column separation and concentration by magnetization on a small-sized surface | 0.005 | 0.5 |

By way of comparison, the limit of detection obtained on automated machines for immunoanalysis is of the order of a few pg/ml depending on the cases. A gain in sensitivity by a factor of about 100 to 1000 is therefore obtained using the method according to the present invention.

Example 8

Synthesis of the Conjugated Particles of Gold-anti-TSH Antibody

The example below shows that the method according to the invention can be used and extended to particles of support which are nonmagnetic and of a different nature.

Solution of colloidal gold. The pH of the solution of colloidal gold (diameter of the particles: 15 nm, Polyscience, OD$_{520}$=0.524), is adjusted to 7.2 with a 0.2 M K$_2$CO$_3$ solution. The colloidal gold is then filtered on a 0.1 $\mu m$ membrane.

Solution of ligand. The anti-TSH antibodies are dialyzed in 2 mM borate buffer pH 9.00, and then filtered on a 0.1 $\mu m$ membrane, just before use, in order to remove the possible aggregates, and assayed at 280 nm.

Synthesis of the protein/gold conjugated particles. The antibody solution is added to the gold solution, with stirring, at a concentration of 8 $\mu g$ of antibody/ml of colloidal gold. After incubating for 10 minutes, colloidal stabilization is ensured by addition of a bovine serum-albumin (BSA) solution at 10 mg/ml in PBS, in order to obtain a final concentration of conjugated particles of 100 μg/ml. The solution is filtered (0.1 μm), and then purified on a membrane with a cut-off MWCO=300,000, in order to remove the excess of antibodies. The conjugated particles are taken up in PBS/BSA/Tween 20 0.5% medium, and filtered. They are stored at 4° C. in the presence of sodium azide (0.05%) and can be stored for several months. The sodium azide may be optionally replaced by a sterilizing filtration at the time of use.

Example 9

Sandwich Assay of the TSH by the Conjugated Particles Labeled With Colloidal Gold: Comparison of the Methods With and Without Enrichment by Centrifugation of the Intermediate Medium Without enrichment On plates as obtained in Example 1, 70 μl of TSH solution of increasing concentration from 0 to 50 ng/ml of PBS/Tween 0.5% are deposited on the plates and incubated for one hour at 37° C. After rinsing with PBS/Tween, 70 μl of solution of conjugated particles ($OD_{520\ nm}$=1.4) are incubated for 1 h at 37° C. The plates are then washed, dried and analyzed by AFM. The number of complex particles per unit of surface is counted.

With enrichment by centrifugation

After synthesis of the conjugated particles (reagent) described above, 100 μl of conjugated particles ($OD_{520\ nm}$=1.4) and 6 ng of TSH are incubated in variable volumes from 0.1 to 10 ml of PBS/Tween 0.5% containing 0.1 mg/ml of BSA. The solutions obtained are incubated overnight at 370° C., with stirring. Controls without antigen (analyte) are prepared. After the incubation, the solutions are enriched by washing and membrane filtration (MWCO=100,000) in order to obtain a final volume of a few tens of μl. They are then deposited on plates as obtained in Example 1. The incubation takes place for 1 h at 37° C. The rinsing and the analysis take place as above.

Figure 17:
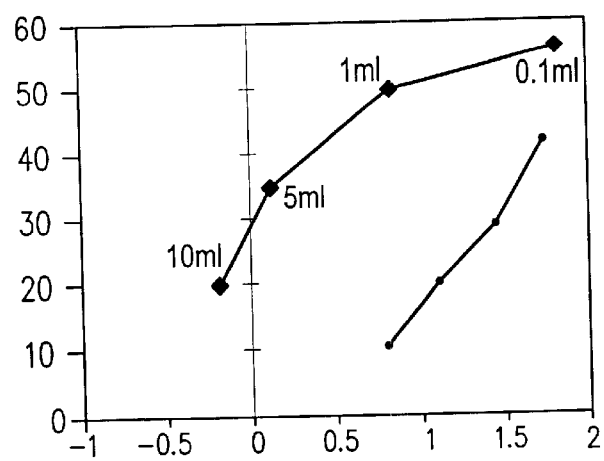
FIG. 17 shows a comparison of the various modes of enrichment, using colloidal gold particles as a support belonging to the reagent. The numrber of particles per $\mu m^2$ is represented on the y-axis, the THS concentration (Log 10 ng/ml) on the x-axis. The black diamonds refer to a determination after enrichment by centrifugation, and the black circles to a determination without enrichment by centrifugation.

The results are presented in FIG. 17. A clear improvement in the sensitivity at equivalent TSH concentration is observed when the complex particles are concentrated.

Example 10

Manufacture of the Biospecific Supports (other supports and receptors) by Coupling of Oligonucleotides (ODN)

The silica surfaces are cleaned with sulfochromic acid (2 h, 120° C.) and then silanized with aminopropyldimethylethoxysilane (2% in anhydrous toluene) for 2 h at room temperature. A copolymer, maleic anhydride-co-methyl vinyl ether (MAVE, Mn=20,000), capable of establishing covalent bonds with amine functions, is then grafted on the amine-containing surfaces. A solution containing 1 mg of MAVE/10 ml of anhydrous DMSO is prepared just before use. The amine-containing surfaces are immersed in this solution and incubated, with stirring, for 1 h at room temperature in the presence of triethylamine (1% v/v). They are then rinsed with DMSO and dried with nitrogen.

A solution of capture ODN (17 bases) is prepared at a concentration of 8 μM in a 0.1 M sodium borate, 0.5 M NaCl (5%)/DMSO (95%) mixture. 50 μl of solution are deposited on the plate and incubated for 1 h at 37° C. The supports are then rinsed in PBS-Tween. Next, 50 μl of a solution of PEG are deposited on the surface and incubated for 30 minutes in order to avoid nonspecific interactions. The surfaces are rinsed with PBS/Tween. Such surfaces are called hereinafter "biospecific surfaces".

Example 11

Manufacture of the Magnetic Particles/ODN Biotin Detection Conjugates

Example 11a

100 μl of magnetic particles coated with streptavidin (Immunicon) are added to 100 μl of a solution of the biotinylated detection ODN (21 bases) (8.37 pmol/μl). This solution is incubated for 1 h at 37° C., with stirring. The excess of ODN is removed by 3 successive magnetization/dilution steps and the conjugates are finally taken up in 100 μl of PEG buffer.

Example 11b

100 μl of magnetic particles coated with streptavidin ($10^{11}$ particles, that is to say $5 \times 10^{12}$ particular, in the lower part 20, the addition, to the surface of the magnet, of a pointed part of a so-called "soft" magnetic material having the property of driving and confining the magnet field lines to the end of this tip. This part or the equivalent may equally well be added to the embodiments according to the examples molecules of streptavidin, Miltenyi Biotec) are added to the solution of the biotinylated detection ODN (28 bases) ($4 \times 10^{13}$ molecules), carrying a spacer strand of eight bases. This solution is incubated for 1 h at 37° C., with stirring. The excess of ODN is removed by passing over an HGMS separation column and then taken up in 100 μl.

The two reagents thus obtained are called hereinafter "detection conjugates"

Example 12

Capture of DNA Targets (analyte) by the Detection Conjugates of Example 11a

20 μl of the solution of detection conjugates as described in Example 11a are diluted in PEG buffer. The targets (37 bases, $8.23 \times 10^{13}$ copies/μl), carrying the sequences respectively complementary to the capture and detection ODN, are added in the quantity desired for a total volume of 1 ml. The mixture is incubated for 2 h at 37° C., with stirring. The complexes formed will be used as they are.

Example 13

Concentration of targets (analyte) With the Aid of the Detection Conjugates of Example 11a. Influence of the Presence of the Magnet 2 biospecific supports are prepared. Also, 2 samples, each containing $10^{12}$ copies/ml, are incubated in the presence of detection conjugates as described in Example 11a. The biospecific supports are placed at the bottom of a vessel. One of these vessels is placed on a magnet consisting of rare earths (diameter 6 mm, height 6 mm, B=0.32 Tesla). The solution containing the targets hybridized with the magnetic particles is deposited in the vessels, and incubated for 1 h, with stirring, by pipetting every 10 min. After the incubation, the supports are rinsed in PBS-Tween and then in 0.1 M ammonium carbonate buffer, before being dried and analyzed in contact with air mode by AFM.

In a useful zone of 4×4 μm of the biospecific surface, 0.3 particle per μm² is detected without a magnet, and 86 particles per μm² with a magnet.

Example 14

Concentration of Targets (analyte) With the Aid of Detection Conjugates of Example 11a. Determination of the Limit of Detection The targets are practically not detected in the absence of the magnet, whereas a monolayer of particles is obtained in the presence of the magnet, corresponding to the saturation of the signal.

Several biospecific supports are prepared. Increasing concentrations of targets (between 0 and $8\times10^{12}$ targets/ml) are prepared in 1 ml of PEG buffer. The capture of the DNA targets by the detection conjugates as described in Example 11a is carried out as described in Example 12. After the incubation, the biospecific supports are placed on magnets as described in Example 12, at an incubation temperature of 37° C. 100 $\mu$l of the solutions containing the targets hybridized with the detection conjugates are deposited on the biospecific supports. The solution is incubated for 3 minutes and then the supernatant is removed. 100 $\mu$l are again deposited, and then the drop is stirred by pipetting in order to resuspend the particles. This protocol is repeated until all the solution has been concentrated on the support ($10\times100$ $\mu$l). After the incubation, the surfaces are rinsed with PBS-Tween and then with 0.1 M ammonium carbonate buffer, before being dried and analyzed in contact with air mode by AFM. The density of the particles is measured in the maximum magnetization zone. The level of covering of the particles on the images is determined by the use of image processing software.

The sensitivity limit is estimated at $7\times10^8$ targets/ml, that is to say a gain by a factor of 100 relative to the detection of DNA targets by a conventional enzymatic test, of the ELOSA type (Enzym Linked Oligo Sorbent Assay), without concentration ($8\times10^{10}$ targets/ml), carried out on the same support.

Example 15

Concentration of Targets (analyte) With the Aid of the Detection Conjugates of Example 11b. Dotermnation of the Limit of Detection 50 $\mu$l of the solution of detection conjugates as described in Example 11b are diluted in PEG buffer. The targets (37 bases), carrying the sequences respectively complementary to the capture and detection ODN, are added in the desired quantity for a total volume of 1 ml. The mixture is incubated overnight at 37° C., with stirring. The detection conjugate-target complexes are then purified on an HGMS separation column as described in Example 3, in order to obtain a final volume of 100 $\mu$l.

Sever al biospecific supports are prepared. They are placed on magnets as described in Example 13, at an incubation temperature of 37° C. The solution of detection conjugate-target complexes is incubated for 30 minutes with stirring by pipetting every 10 minutes. After the incubation, the surfaces are rinsed with PBS-Tween and then 0.1 m ammonium carbonate buffer, before being dried and analyzed in contact with air mode by AFM.

The limit of detection is estimated at $3\times10^9$ copies/ml, that is to say a gain by a factor of 30 with respect to the ELOSA test carried out on the same support without concentration.

Example 16

Comparison of the Concentrating System in Solution, With Respect to a Sequential Incubation of the Reagents at the Surface Assay 1: the targets are captured in solution as described in Example 15.

Assay 2: after preparation of the biospecific supports, 100 $\mu$l of a solution of targets (between 0 and $8\times10^{13}$ targets/ml) are incubated on the support (particles) which is then rinsed with PBS-Tween. Next, 100 $\mu$l of solution of biotinylated ODNs (0.5 $\mu$M in PEG) are incubated. Finally, the support is placed on a cylindrical magnet as described in Example 13, and 100 $\mu$l of a commercially available solution of magnetic particles coated with streptavidin (Miltenyi Biotec) and diluted one-half with the PEG buffer are incubated for 30 minutes with stirring every 10 minutes.

The detection limit of the sequential system at the surface is estimated at $7.6\times10^{10}$ targets/ml, whereas that of the assay in solution was estimated in Example 15 at $3\times10^9$ copies/ml. The amplification factor linked to the incubation of the targets and of the conjugates in solution is therefore 25.

Example 17

Advantage of the Flow-through Cell

With the Aim of Concentrating Magnetic Conjugates

Figure 23:
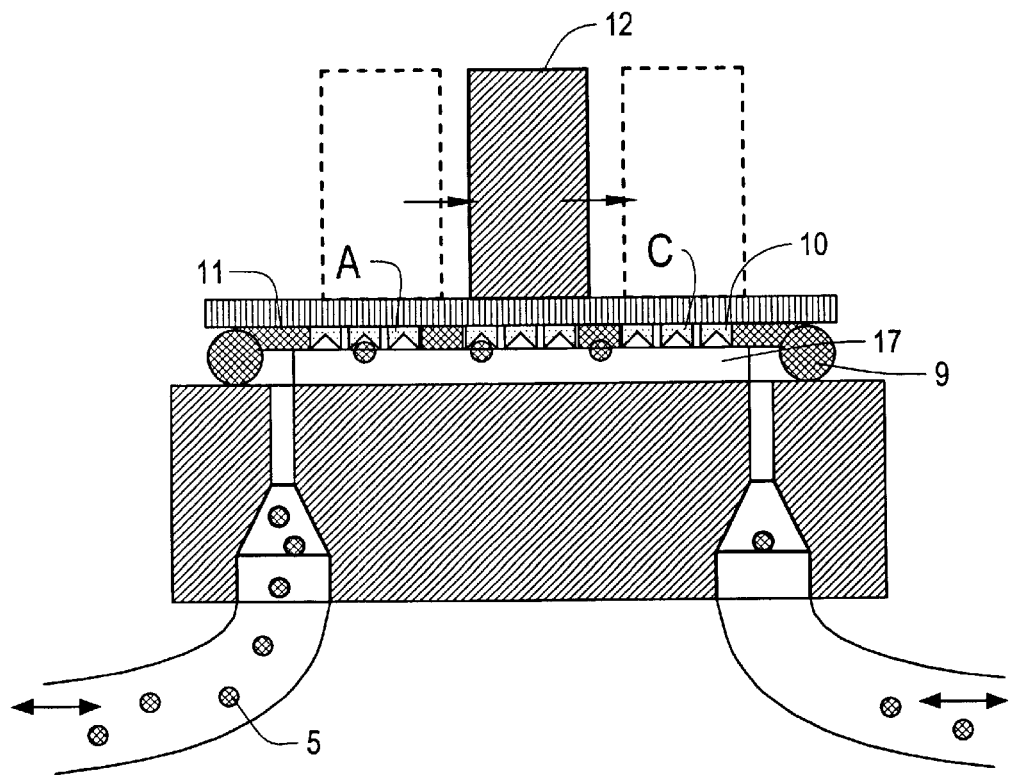
FIGS. 23 and 24 represent the embodiment described in FIG. 22 to which there have been added two means of concentrating, and a biospecific surface containing several useful zones as described in FIG. 20, for example.

This assay illustrates another method of carrying out the invention represented in FIGS. 23 and 24.

Biospecific supports are prepared by adsorbing biotinylated (positive control) or nonbiotinylated (negative control) antiferritin antibodies at a concentration of 0.2 $\mu$l/ml on silica surfaces.

Assay 1: These supports are placed in the cell containing a cylindrical magnet as defined above, surmounted by a truncated cone 0.5 mm in diameter at its summit. A solution containing 30 $\mu$l of magnetic particles coated with streptavidin (Miltenyi Biotec), diluted in 1 ml of PBS/Tween/BSA buffer (0.1 mg/ml), is injected onto each support at a flow rate of 0.017 ml/min. After this incubation, the supports are rinsed, dried and analyzed by AFM.

Assay 2: In parallel, assays are carried out on these same biological supports outside the cell. Each support is placed on a cylindrical magnet as defined above. A solution containing 30 $\mu$l of magnetic particles coated with streptavidin (Miltenyi Biotec), diluted in 60 $\mu$l of PBS-Tween-BSA buffer is prepared and deposited on the supports, and then incubated for 30 minutes by stirring every 10 minutes. After this incubation, the supports are rinsed, dried and analyzed by AFM and the level of covering of the particles is evaluated.

It is observed i) that the specific signal (97+/−3 for Assay 1, 63+/−16) for Assay 2 and ii) and the signal/noise ratio (139 for assay 1, 31 for assay 2) are markedly improved during the use of the flow-through cell.

In summary, the examples described above embody the general method according to the invention. Example 7 shows that the invention makes it possible to detect analyte concentrations as low as 5 fg/ml of TSH, which corresponds to $1.2\times10^5$ molecules. A bacterium represents about $10^4$ to $10^5$ molecules of ribosomal RNA. Examples 10 to 16 show that methods of implementation, which are identical or different, can be used for the detection of DNA targets. Consequently, with an implementation of the same type, it appears possible to detect from 1 to 10 bacteria per unit of volume. Associated with a method of concentration as described and applied to nucleic material, the analytical sensitivity of the method according to the invention is therefore of the same order as that of methods of amplification such as PCR, NASBA, and the like.

Figure 18:
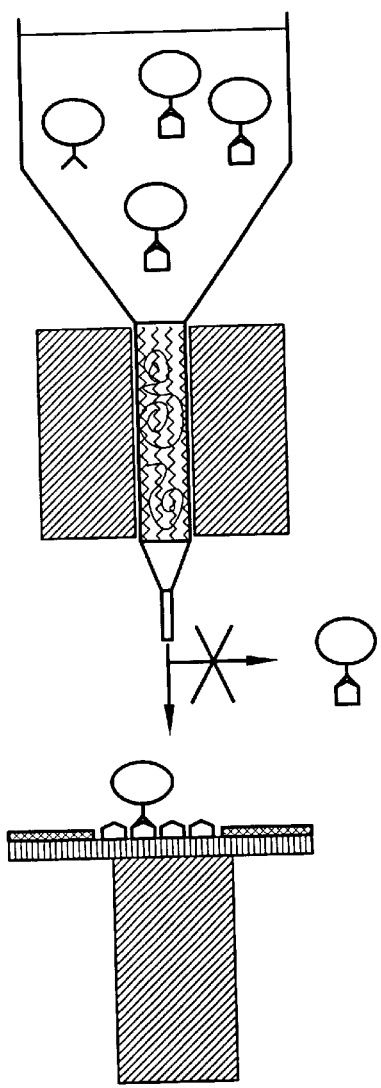
FIG. 18 represents an embodiment of the invention for the assay of haptens by competition and FIG. 19 the expected theoretical curve, expressing, on the y-axis, the number of particles detected per unit of biospecific surface, and, on the x-axis, the original hapten concentration.
Figure 19:
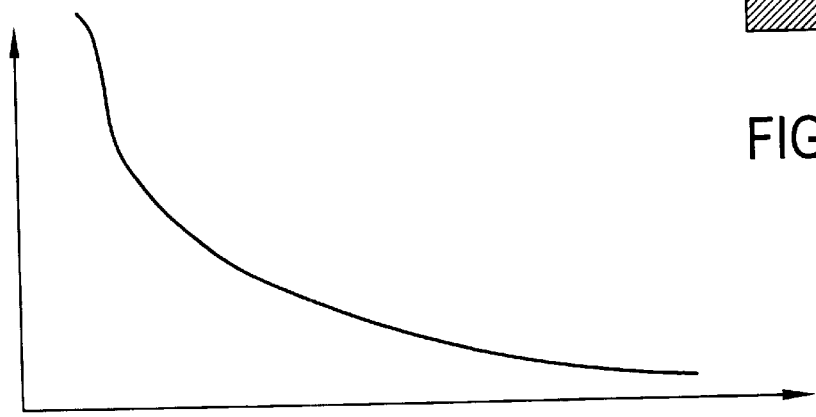

The embodiments of the invention may be many and, without being limiting, a few examples thereof may be given:

The invention may be applied to the assays of haptens by competition according to an example of a method described in FIG. 18. Haptens are immobilized on a limited surface. The solution containing haptens to be assayed (analyte) is placed in contact with conjugated particles carrying only one anti-hapten antibody (receptor) as described in Example 3, for a sufficient time for the complex particles to form. The complex particles are separated according to one of the methods described and concentrated on the useful surface carrying the receptor haptens. The conjugated particles which have previously reacted with a hapten in solution cannot bind and are removed by washing. The conjugated particles which have not reacted, carrying the available antibody may, in contrast, react with the receptor haptens of the biospecific useful surface and be detected by one of the various means described above. The number of conjugated particles detected decrease when the hapten concentration in solution increases, as is represented on the theoretical curve of FIG. 19.

As described in the documents U.S. Pat. No. 5,543,289 or U.S. Pat. No. 5,169,754, cells may be separated from a solution by magnetic sorting. Following this operation, it is possible to concentrate the labeled analyte (cells, yeasts, bacteria, viruses or phages) and to retain it on a small-sized biospecific surface, by a receptor different from or identical to that which allowed the production of the complex particles, by a method as described in FIG. 10, for example. The determination (detection and/or quantification) may be made by any appropriate means, such as intrinsic or extrinsic fluorescent markers, microscopy methods, and the like, including the detection by the use of particles which have served for the separation and concentration.

Figure 20:
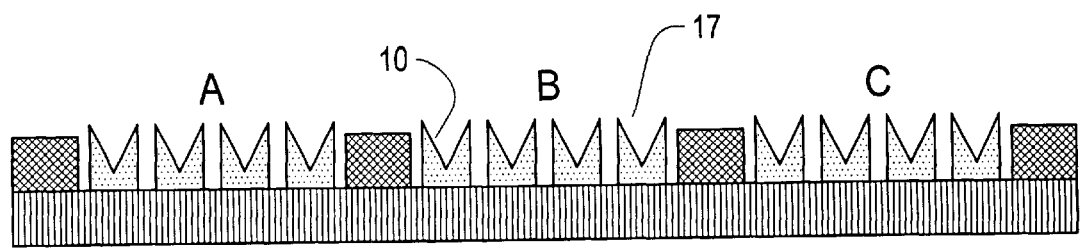
FIG. 20 represents an accessible biospecific surface of the capture support, containing several useful zones with respectively different affinity receptors.
Figure 21:
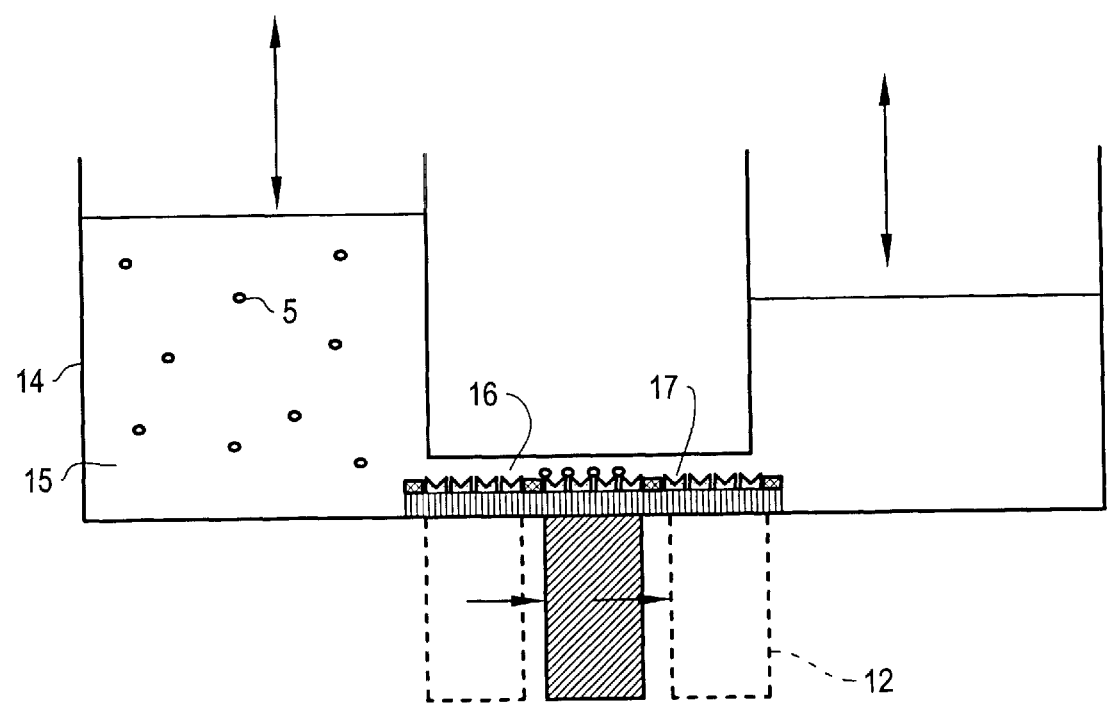
FIG. 21 represents another embodiment of the invention.
Figure 22:
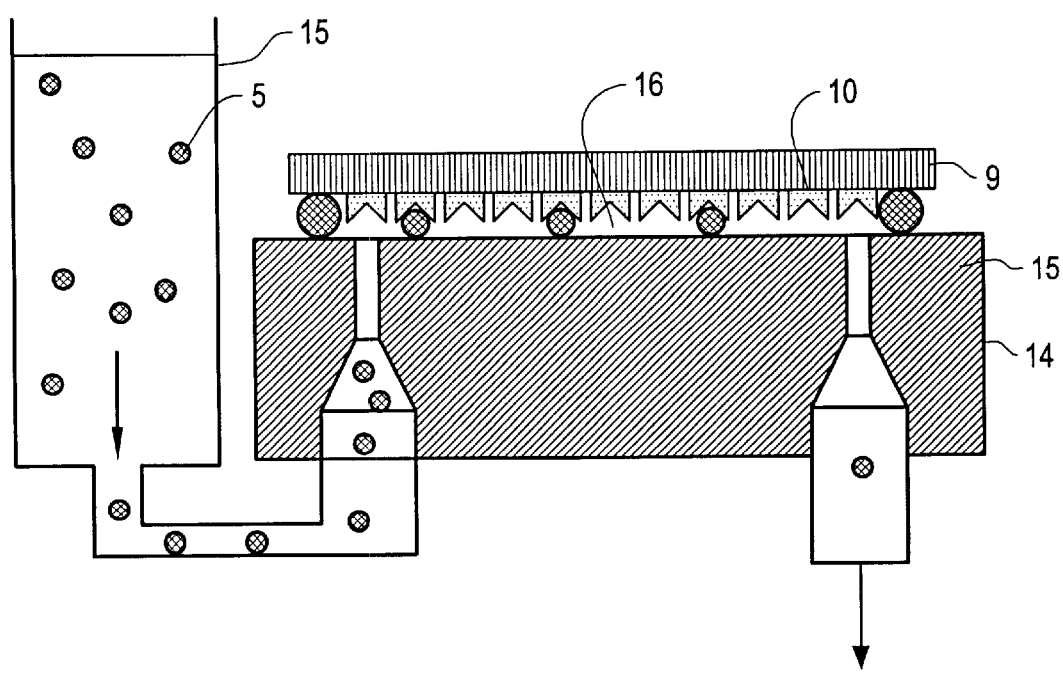
FIG. 22 represents another embodiment of the invention.

Specific embodiments, intended in particular to bind several ligands having different affinities on the same limited surface (multiaffinity), and/or to concentrate the conjugated particles at desired locations makes it possible to apply the invention to a multiple detection. An example is described in FIG. 20; in this case, the useful surface comprises three useful zones A, B and C comprising three receptors which are respectively different, and situated at three identified geographic positions. Using a specific method of implementation, as described in FIG. 21, conjugated particles are immobilized on their specific receptors. The method comprises a device 14 which comprises a compartment 15 in which the formation of the complex particles 5 takes place. This compartment may comprise a system for mechanical stirring, or, if the particles used are magnetic, a magnetic field stirring system. After a sufficient time for the formation of the complex particles, these are brought into contact with the surface 17 (mono or multiaffinity) via a channel 16; the latter, of low height, is intended to limit the height of the solution above said surface, thus limiting the distance which a complex particle has to travel before being captured by its specific receptor. The probability of a complex particle/receptor reaction may be advantageously improved by recirculating the solution on the limited surface. The device describes the use of a magnet 12 which moves from one position to the next (for example, from zone A to zone B, then to zone C). A single magnet occupies, according to another variant, the entire surface, or several magnets, each facing a zone A, B or C, without this changing the method of the invention. The device described may consequently be used for the multidetection of analytes, or for the screening of libraries (phage libraries, for example).

The devices described above can be used according to techniques derived from microtechnologies.

What is claimed is:

1. A method for at least one of isolating, detecting and quantifying at least one analyte distributed in a dilute liquid medium, comprising the following steps:
   a) providing (i) a first reagent comprising particles of a first support distributed in the liquid medium and at least one first receptor for an analyte fixed on said particles; and (ii) a capturing means comprising a second support having an exposed surface defining at least one active zone and at least one second receptor for said analyte or for said first reagent, said second receptor being fixed in said active zone;
   b) contacting a liquid sample obtained from the medium containing the analyte with said first reagent to obtain an intermediate reagent comprising particles of a complex distributed in another liquid medium, said complex being the reaction product of at least part of said first reagent with said analyte;
   c) contacting the capturing means with at least one capture partner selected from the group consisting of the part of the first reagent that was not reacted with said analyte during step (b) and the intermediate reagent and binding the capture partner to the active zone; and
   d) increasing the quantity of capture partners exposed per unit of surface of the active zone, wherein a concentrated deposit of the capture partner is immobilized in the active zone, whereby small quantities of analyte in said dilute medium are isolated, detected or quantified.

2. The method according to claim 1, wherein the capture partner concentration level is determined so that the quantity of said immobilized capture partner remains at most equal to the quantity of said second receptor on said second support.

3. The method according to claim 2, wherein the first reagent comprises particles of the first support conjugated with the first receptor having the capacity to be separated from any liquid medium in which they are dispersed, under the action of a physical means applied to the liquid medium, said method further comprising applying said physical means to at least part of the intermediate medium to separate said complex particles, optionally washing said separated complex particles and eluting said complex particles by ending the application of said physical means to increase the ratio of concentration of the capture partner to said deposit in said active zone.

4. The method according to claim 3, wherein the particles of the first support are magnetic or superparamagnetic and the physical means comprise a magnetic field applied to the intermediate medium.

5. The method according to claim 3, wherein said particles are non-magnetic and said physical means are selected from the group consisting of: electrical, gravity, and centrifugation.

6. The method according to claim 4, wherein said physical means applied to said magnetic particles is High Gradient Magnetic Separation (HGMS) technique.

7. The method according to claim 1, wherein said first receptor and said second receptor contain the same ligand immobilized respectively on said first support and said second support.

8. The method according to claim 1, wherein the first reagent comprises particles of the first support conjugated with the receptor having the capacity to be separated from any liquid medium in which they are dispersed under the action of a physical means applied to said liquid medium, said physical means applied in relationship with said second support, to concentrate said deposit in said active zone.

9. The method according to claim 1, wherein the first reagent is labeled and the treatment of the analyte comprises a step of determining the marker for the deposit, which is concentrated and immobilized in said active zone of said second support.

10. The method according to claim 9, wherein the mode of labeling of the first reagent is selected from the group consisting of:

the support itself is a marker;

a marker is bound to said support; and a marker is bound to said receptor.

11. The method according to claim 9, wherein the analyte is determined from the deposit concentrated in said active zone by the method selected from the group consisting of topographical methods, magnetic methods, electrical methods, optical methods and methods for measuring mass variations.

12. The method according to claim 11, wherein the active zone is designed so that the quantity of the deposit immobilized on said second support is at least equal to the sensitivity threshold of the method of determination, expressed as number of particles per unit of surface.

13. The method according to claim 11, wherein said topographical methods comprises: atomic force microscopy (APM) or profilometry.

14. The method according to claim 11, wherein said electrical methods comprises: measurement of a variation in capacitance or resistance, tunneling microscopy, or impedance measurements.

15. The method according to claim 11, wherein said optical methods comprise measurement of the refractive index or the measurement of light intensity.

16. The method according to claim 11, wherein methods for measuring mass variations comprise quartz crystal microbalance.

17. The method according to claim 1, wherein the capture partner is said intermediate reagent and the amount of analytes is determined by a direct assay format.

18. The method according to claim 1, wherein the capture partner is said first reagent and the amount of analytes is determined by a competitive assay format.

19. The method according to claim 1, wherein another sample is obtained by enriching said intermediate medium with complex and said other sample is brought into contact with the accessible surface of said second support.

20. The method according to claim 19, wherein said other sample is brought into contact with the accessible surface of said second support by depositing a measured quantity of said other sample on the accessible surface.

21. The method according to claim 19, wherein said other sample is brought into contact with said accessible surface of said second support by passing a stream of said other sample, of a relatively small thickness, optionally recycled, in contact with said accessible surface.

22. The method according to claim 1, wherein the liquid medium contains a plurality of various analytes, wherein the accessible surface of said second support comprises a plurality of active zones, having a plurality of different receptors for different capture partners.

* * * * *